United States Patent [19]
Gethöffer et al.

[11] Patent Number: 5,292,451
[45] Date of Patent: Mar. 8, 1994

[54] UREIDOPEROXYCARBOXYLIC ACIDS AND PREPARATION AND USE THEREOF

[75] Inventors: Hanspeter Gethöffer, Frankfurt am Main; Gerd Reinhardt, Kelkheim (Taunus); Peter Naumann, Taunusstein, all of Fed. Rep. of Germany

[73] Assignee: Hoechst Aktiengesellschaft, Frankfurt, Fed. Rep. of Germany

[21] Appl. No.: 893,772

[22] Filed: Jun. 5, 1992

Related U.S. Application Data

[62] Division of Ser. No. 703,461, May 21, 1991, Pat. No. 5,149,864.

[30] Foreign Application Priority Data

May 25, 1990 [DE] Fed. Rep. of Germany ... P4016980.4

[51] Int. Cl.$^5$ .............. C01B 15/00; C11D 7/54; C11D 7/38
[52] U.S. Cl. ............. 252/186.42; 252/186.26; 252/95; 252/99; 562/2
[58] Field of Search ............ 252/186.42, 186.26

[56] References Cited

U.S. PATENT DOCUMENTS

| | | | |
|---|---|---|---|
| 2,717,908 | 9/1955 | Snyder et al. | 562/560 |
| 4,221,675 | 9/1980 | Schirmann et al. | 252/186.38 |
| 4,248,928 | 2/1981 | Gianfranco et al. | 428/286 |
| 4,909,953 | 3/1990 | Sadlowski et al. | 252/99 |
| 5,049,298 | 9/1991 | Plouman et al. | 252/95 |

FOREIGN PATENT DOCUMENTS

| | | |
|---|---|---|
| 0105689 | 4/1984 | European Pat. Off. |
| 0127780 | 12/1984 | European Pat. Off. |
| 0170386 | 2/1986 | European Pat. Off. |
| 3438529 | 4/1986 | Fed. Rep. of Germany |

*Primary Examiner*—Richard D. Lovering
*Assistant Examiner*—Joseph D. Anthony
*Attorney, Agent, or Firm*—Connolly & Hutz

[57] ABSTRACT

Compounds of the formula

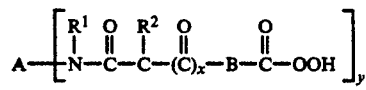

where
y is 1 or 2,
A is hydrogen, $C_1$–$C_2$-alkyl, aryl or a group of the formula

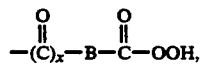

if y is 1, or $C_2$–$C_{20}$-alkylene or arylene if y is 2,
$R^1$ and $R^2$ can be identical or different and each is hydrogen, $C_1$–$C_{20}$-alkyl, aryl, haloaryl, alkoxyaryl or alkylaryl, or else $R^1$ and $R^2$ together are a $C_2$–$C_4$-alkylene radical,
x is 0 or 1,
B is a group of the formula

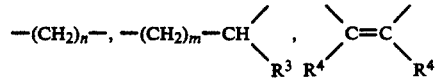

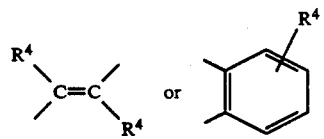

n is from 1 to 20,
m is 0, 1 or 2,
$R^3$ is $C_1$–$C_{20}$-alkyl and
$R^4$ is in each case hydrogen or $C_1$–$C_{20}$-alkyl.

These compounds are suitable for use as bleaching, oxidizing or disinfecting agents.

6 Claims, No Drawings

UREIDOPEROXYCARBOXYLIC ACIDS AND PREPARATION AND USE THEREOF

This is a divisional application of U.S. Ser. No. 07/703,461 filed May 21, 1991, now U.S. Pat. No. 5,149,864.

DESCRIPTION

Inorganic per-salts have long been used as bleaching additives in detergents. However, since they develop their maximum bleaching power only at temperatures above 60° C., organic compounds are used for activating them. These organic compounds react with hydrogen peroxide during the wash to liberate a peroxycarboxylic acid which has a bleaching effect at a temperature as low as 40°-60° C. A long list of known perborate activators such as N-acyl compounds (tetraacetylethylenediamine, tetraacetylmethylenediamine, tetraacetylglycoluril) or activated esters (pentaacetylglucose, sodium acetoxybenzenesulfonate, sodium benzoyloxybenzenesulfonate) is given for example in U.S. Pat. No. 4,248,928.

In addition, a number of organic peroxycarboxylic acids have recently been described for use as bleaching systems for detergents. These include not only already commercially available peroxycarboxylic acids such ad dodecanediperoxycarboxylic acid (EP 127 782) and monoperoxyphthalic acid (EP 27 693) but also persuccinic acid (DE 34 38 529), perglutaric acid (DE 35 39 036) and sulfoperbenzoic acid. However, the problem with these peroxycarboxylic acids is their short shelf life, which in some instances necessitates separate physical or chemical stabilization. Of particular use is the preparation of magnesium salts (EP 105 689) or an addition of phosphane oxide/sodium sulfate (DE 33 20 497). Organic peroxycarboxylic acids can also be stabilized by an additional amide group in the molecule (EP 170 386) or else by an additional imide group in the molecule (EP 349 940). In addition, numerous further peroxycarboxylic acids with stabilizing functional groups have been described, for example ammonium peroxycarboxylic acids (EP 316 809), pyridine N-oxide peroxycarboxylic acids (EP 300 461) or sulfone peroxycarboxylic acids (EP 267 175).

The present invention relates to peroxycarboxylic acids of the formula

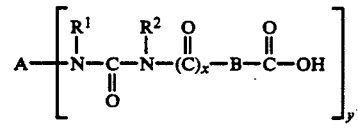

where
y is 1 or 2,
A is hydrogen, $C_1$–$C_2$-alkyl, aryl, preferably phenyl, or a group of the formula

if y is 1, or $C_2$–$C_{20}$-alkylene or arylene, preferably phenylene, if y is 2,
$R^1$ and $R^2$ can be identical or different and each is hydrogen, $C_1$–$C_{20}$-alkyl, aryl, preferably phenyl, or haloaryl, preferably chlorophenyl, or alkoxyaryl, preferably $C_1$–$C_4$-alkoxyphenyl, or alkylaryl, preferably $C_1$–$C_4$-alkylphenyl, or else $R^1$ and $R^2$ together are a $C_2$–$C_4$-alkylene radical,
x is 0 or 1,
B is a group of the formula

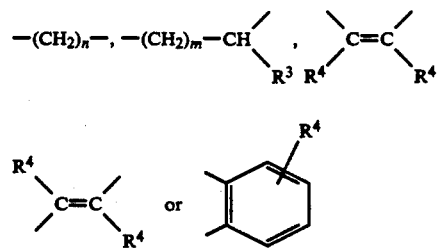

n is from 1 to 20,
m is 0, 1 or 2,
$R^3$ is $C_1$–$C_{20}$-alkyl and
$R^4$ is in each case hydrogen or $C_1$–$C_{20}$-alkyl.

Particular preference is given to N-carbamoyl-6-aminoperoxyhexanoic acid, N-carbamoyl-11-aminoperoxyundecanoic acid, N-(N'-phenylcarbamoyl)-6-aminoperoxyhexanoic acid, N-carbamoylperoxysuccinamic acid, N-(N'-butylcarbamoyl)-peroxysuccinamic acid, N-carbamoylperoxyglutaramic acid and N-(N'-butylcarbamoyl)peroxyglutaramic acid.

The ureidoperoxycarboxylic acids are prepared by the steps of: -a- synthesizing the ureidocarboxylic acids, -b- oxidizing to obtain a ureidoperoxycarboxylic acid, -c- isolating the ureidoperoxycarboxylic acid.

In what follows, the individual steps will be explained in more detail. The preparation of the ureidocarboxylic acids

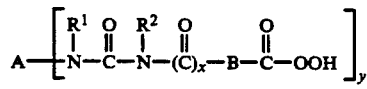

can be effected by synthesis steps known per se. The compounds where y is 1 and x is 0 are obtained by reacting potassium isocyanate or isocyanates of the formula $$R^1-N=C=O$$

with aminocarboxylic acids of the formula

and compounds where y is 2 and x is 0 are obtained by reacting diisocyanates of the formula $$O=C=N-A-N=C=O$$

with two equivalents of aminocarboxylic acid (see Houben-Weyl, Methoden der Organischen Chemie, VIII, p. 157). Ureidocarboxylic acids where y is 1 and x is 1 are obtainable by syntheses starting from anhydrides of the formula

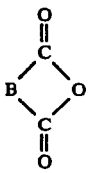

and urea or substituted ureas of the formula

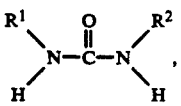

while ureidocarboxylic acids where y is 2 and x is 1 are obtainable by using two equivalents of anhydride per equivalent of urea or substituted urea (see U.S. Pat. No. 2,717,908, DP 945 234).

Usable isocyanates are in particular phenyl isocyanate, p-tolyl isocyanate and hexamethylene diisocyanate, usable aminocarboxylic acids are in particular glycine, α- and β-alanine, ε-aminocaproic acid and ω-aminoundecanecarboxylic acid, usable anhydrides are in particular succinic anhydride, glutaric anhydride, maleic anhydride, phthalic anhydride, and alkylsuccinic anhydride, and usable urea compounds are in particular urea, N-butylurea, N-octylurea and N-phenylurea.

The conversion of the ureidocarboxylic acids obtained in step -a- into ureidoperoxycarboxylic acids is effected by reaction with an oxidizing mixture of hydrogen peroxide and a strong acid. The hydrogen peroxide is used in the form of a from 30 to 95 percent strength by weight, preferably from 50 to 85 percent strength by weight, aqueous solution. Suitable acidic catalysts are sulfuric acid, methanesulfonic acid or an acidic ion exchange material. Sulfuric acid is used in the form of a from 50 to 96 percent strength by weight, preferably from 75 to 96 percent strength by weight, aqueous solution.

Hydrogen peroxide is used per oxidizable carboxyl group in the ureidocarboxylic acid in a molar ratio of from 10 to 1:1, preferably from 4 to 2:1. The identity and amount of the catalyst acid depend on the ureidocarboxylic acid used. In general, from 2 to 6 times the weight, based on the ureidocarboxylic acid, is added of catalyst acid. The reaction temperature depends on the stability of the corresponding ureidoperoxycarboxylic acid, and is between 5° and 30° C., preferably from 10° to 20° C.

The claimed ureidoperoxycarboxylic acids generally precipitate on addition of water and are simple to isolate by filtration or centrifugation. It is also possible to precipitate ureidoperoxycarboxylic acids which do not precipitate in full or at all on addition of water by adding aqueous solutions of basic salts.

The ureidoperoxycarboxylic acids of the present invention are solid and almost odorless, they have a low vapor pressure and possess excellent thermal stability. They can be used as solutions, powders or in processed form alone or combined with other substances for bleaching, oxidizing or disinfecting purposes.

EXAMPLES

Example 1

N-Carbamoyl-11-aminoperoxyundecanoic acid 61.6 g (0.25 mol) of N-carbamoyl-11-aminoundecanoic acid are dissolved in 74.4 g of sulfuric acid (96% strength by weight) and the solution is cooled to 15° C. 23.8 g (0.6 mol) of hydrogen peroxide (85% strength by weight) are added dropwise with cooling at such a rate that the internal temperature can be maintained between 15 and 20° C. The reaction mixture is subsequently stirred with occasional cooling at 20° C. internal temperature for 1 h and then cooled down to 10° C., 200 ml of water are added dropwise, and the precipitated peroxycarboxylic acid is filtered off with suction. The filter cake is washed with water until free of mineral acid and is dried at 40° C. under an aspirator vacuum.

Yield: 63.3 g (96.5%) of white odorless crystals.
Active oxygen content: 5.8% (94.6%).
Melting point: 99°–101° C.

Example 2

N-Carbamoyl-6-aminoperoxyhexanoic acid 17.4 g (0.1 mol) of N-carbamoyl-6-aminohexanoic acid are dissolved in 50 g of methanesulfonic acid and the solution is cooled to 15° C. 12 g (0.3 mol) of hydrogen peroxide (85% strength by weight) are added dropwise with cooling at such a rate that the internal temperature can be maintained between 15° and 20° C. The mixture is subsequently stirred at 18° C. for a further 10 minutes, then cooled down to 0° C. and adjusted to pH 3 with aqueous sodium hydroxide solution (33% strength by weight). 65 g of sodium hydroxide solution are used. After stirring for 20 minutes at 0° C. the precipitated peroxycarboxylic acid is filtered off with suction, washed with ice-water and dried at 40° C. under an aspirator vacuum.

Yield: 16.2 g (85%).
Active oxygen content: 5.0% (60%).

For purification a sample is recrystallized twice from ethyl acetate (15 g of peroxycarboxylic acid to be recrystallized per 1.5 l of ethyl acetate).

Active oxygen content: 7.2% (86%) of white odorless crystals.
Melting point: 160° C.

Example 3

N-Carbamoylperoxysuccinamic acid 80 g (0.5 mol) of N-carbamoylsuccinamic acid are dissolved in 160 g of methanesulfonic acid and the solution is cooled to 15° C. 60 g (1.5 mol) of hydrogen peroxide (85% strength by weight) are added dropwise with cooling at such a rate that the internal temperature can be maintained between 15° and 20° C. The reaction mixture is stirred at 20° C. for 10 minutes, then cooled to 10° C. and admixed with water added dropwise with cooling. The precipitated peroxycarboxylic acid is filtered off with suction, washed free of mineral acid with water and dried at 40° C. under an aspirator vacuum.

Yield: 53.1 g (60.3%) of white crystals.
Active oxygen content: 9% (99%).
Melting point: 176°–179° C.

Example 4

N-Carbamoylperoxyglutaramic acid 11.3 g (0.065 mol) of N-carbamoylglutaramic acid, 21 g of methanesulfonic acid and 7.8 g (0.2 mol) of hydrogen peroxide (85% strength by weight) are reacted and worked up as described in Example 3.

Yield: 8.8 g (71.3%) of white crystals.
Active oxygen content: 8.2% (98%).
Melting point: 130° C.

Example 5

N-Carbamoylperoxydodecylsuccinamic acid 6.1 g (0.019 mol) of N-(carbamoyl)dodecylsuccinamic acid, 30 g of methanesulfonic acid and 2.3 g (0.056 mol) of hydrogen peroxide (85% strength by weight) are reacted and worked up as described in Example 3.

Yield: 6.2 g (99%) of white crystals.
Active oxygen content: 4.7% (100%).
Melting point: 149° C.

Example 6

N-(N'-Octylcarbamoyl)peroxysuccinamic acid 13.6 g (0.05 mol) of N-(N'-octylcarbamoyl)succinamic acid, 50 g of methanesulfonic acid and 6 g (0.15 mol) of hydrogen peroxide (85% strength by weight) are reacted and worked up as described in Example 3.

Yield: 12.5 g (87%) of white crystals.
Active oxygen content: 5.5% (98.3%).
Melting point: 113° C.

Example 7

N-(N'-Phenylcarbamoyl)-2-aminoperoxypropanoic acid 20.8 g (0.01 mol) of N-(N'-phenylcarbamoyl)-2-aminopropanoic acid, 35 g of methanesulfonic acid and 12 g (0.3 mol) of hydrogen peroxide (85% strength by weight) are reacted and worked up as described in Example 3.

Yield: 19.5 g (87%) of slightly yellow crystals.
Active oxygen content: 6.6% (93%).
Melting point: 147° C.

Example 8

N-(N'-Phenylcarbamoyl)-2-aminoperoxyhexanoic acid 12.5 g (0.05 mol) of N-(N'-phenylcarbamoyl)-6-aminohexanoic acid, 25 g of methanesulfonic acid and 6 g (0.15 mol) of hydrogen peroxide (85% strength by weight) are reacted and worked up as described in Example 3.

Yield: 13.5 g (100%) of white crystals.
Active oxygen content: 5.6% (93%).
Melting point: 102° C.

Example 9

N-(N'-Butylcarbamoyl)peroxyglutaramic acid 80.8 g (0.35 mol) of N-(N'-butylcarbamoyl)glutaramic acid, 123 g of methanesulfonic acid and 42 g (1.05 mol) of hydrogen peroxide (85% strength by weight) are reacted and worked up as described in Example 3.

Yield: 34.6 g (40% of white crystals.
Active oxygen content: 5.4% (83%).
Melting point: 173°–75° C.

Example 10

N-(Carbamoyl)peroxyglutaramic acid 87 g (0.5 mol) of N-(carbamoyl)glutaramic acid, 175 g of sulfuric acid and 102 g (1.5 mol) of hydrogen peroxide (50% strength by weight) are reacted and worked up as described in Example 3.

Yield: 64.5 g (75.8%) of white crystals.
Active oxygen content: 8.1% (96.1%).
Melting point: 133° C.

WASHING TESTS IN LAUNDER-O-METER

The washing tests were carried out in a Launder-o-meter at temperatures of 20°, 40° and 60° C. using water of 15° German hardness. The washing time was 30 minutes. The detergent used was 1.5 g/L of phosphate-containing IEC detergent. The per-acids were used in such amounts that, when completely dissolved, each released 25 mg of active oxygen. The standard soiling used was tea on cotton (WFK) or red wine on cotton (Empa). The bleaching power is reported in terms of the reflectance after the wash.

| | Washing temperature | | |
|---|---|---|---|
| Bleaching system | 20° C. | 40° C. | 60° C. |
| Bleaching results on tea stain | | | |
| Compound of Example 2 | 58.4 | 67.7 | 71.4 |
| Compound of Example 6 | 57.4 | 70.6 | 75.6 |
| Compound of Example 9 | 60.8 | 69.2 | 73.8 |
| Compound of Example 10 | 59.7 | 68.7 | 72.0 |
| TAED/perborate | | 65.7 | 67.9 |
| Perborate | | 58.6 | 62.8 |
| Bleaching results on red wine stains | | | |
| Compound of Example 2 | 63.0 | 70.6 | 75.8 |
| Compound of Example 6 | 62.1 | 71.0 | 79.4 |
| Compound of Example 9 | 64.5 | 72.1 | 77.7 |
| Compound of Example 10 | 64.9 | 71.6 | 76.6 |
| TAED/perborate | | 65.5 | 67.9 |
| Perborate | | 61.2 | 64.6 |

We claim:

1. A bleaching, oxidizing, or disinfecting composition comprising:

a) a compound of the formula

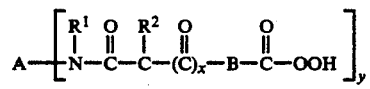

present in a bleaching, oxidizing, or disinfecting amount, where y is 1 or 2,

A is selected from the group consisting of hydrogen, $C_1$–$C_2$-alkyl, aryl and a group of the formula

if y is 1, or, A is selected from the group consisting of $C_2$–$C_{20}$-alkylene and arylene if y is 2, $R^1$ and $R^2$ can be identical or different and each is selected from the group consisting of hydrogen, $C_1$–$C_{20}$-alkyl, aryl, haloaryl, alkoxyaryl and alkylaryl, or else $R^1$ and $R^2$ together are a $C_2$–$C_4$-alkylene radical, x is 0 or 1, B is selected from the group consisting of the formula

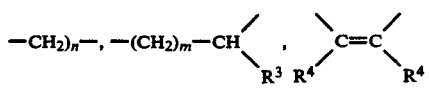

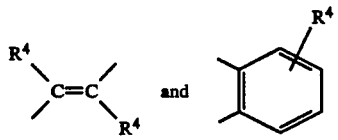

n is from 1 to 20, m is selected from the group consisting of 0, 1 and 2, $R^3$ is $C_1$-$C_{20}$-alkyl and $R^4$ is in each case hydrogen or $C_1$-$C_{20}$-alkyl and b) a detergent.

2. The agent as claimed in claim 1, wherein y is 1 or 2, A is selected from the group consisting of hydrogen, $C_1$-$C_2$-alkyl, phenyl and a group of the formula

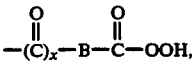

if y is 1, or $C_2$-$C_{20}$-alkylene or phenylene if y is 2, $R^1$ and $R^2$ can be identical or different and each is selected from the group consisting of hydrogen, $C_1$-$C_{20}$-alkyl, phenyl, chlorophenyl, $C_1$-$C_4$-alkoxyphenyl and $C_1$-$C_4$-alkylphenyl, or else $R^1$ and $R^2$ together are a $C_2$-$C_4$-alkylene radical.

3. The agent as claimed in claim 1, wherein y is 1, A is selected from the group consisting of hydrogen, phenyl and $C_1$-$C_2$-alkyl, $R^1$ and $R^2$ are each hydrogen, X is zero or 1, B is a group of the formula —$(CH_2)_n$— and n is from 1 to 20.

4. The composition as claimed in claim 1, wherein $R^1$ and $R^2$ can be identical or different and are selected from the group consisting of phenyl, chlorophenyl, $C_1$-$C_4$-alkoxyphenyl and $C_1$-$C_4$-alkylphenyl.

5. The agent as claimed in claim 1, wherein y is 1, A is selected from the group consisting of hydrogen, phenyl and $C_1$-$C_2$-alkyl, $R^1$ and $R^2$ are each hydrogen, x is zero, B is a group of the formula —$(CH_2)_n$— and n is from 1 to 10.

6. The agent as claimed in claim 5, wherein said n is from 1 to 6.

* * * * *